United States Patent
Fischer et al.

(10) Patent No.: US 12,357,323 B2
(45) Date of Patent: Jul. 15, 2025

(54) SURGICAL INSTRUMENT FOR DRILLING

(71) Applicant: OLOÏDE SA, Etoy (CH)

(72) Inventors: Jean-François Fischer, Etoy (CH); Louis Fischer, Etoy (CH)

(73) Assignee: OLOÏDE SA, Etoy (CH)

( * ) Notice: Subject to any disclaimer, the term of this patent is extended or adjusted under 35 U.S.C. 154(b) by 408 days.

(21) Appl. No.: 17/908,198

(22) PCT Filed: Mar. 4, 2021

(86) PCT No.: PCT/EP2021/055526
§ 371 (c)(1),
(2) Date: Aug. 30, 2022

(87) PCT Pub. No.: WO2021/176022
PCT Pub. Date: Sep. 10, 2021

(65) Prior Publication Data
US 2023/0139621 A1    May 4, 2023

(30) Foreign Application Priority Data
Mar. 4, 2020 (EP) .................................... 20161064

(51) Int. Cl.
*A61B 17/16* (2006.01)
(52) U.S. Cl.
CPC ...... *A61B 17/1624* (2013.01); *A61B 17/1628* (2013.01)
(58) Field of Classification Search
CPC ............ A61B 17/1622; A61B 17/1624; A61B 17/1628
See application file for complete search history.

(56) References Cited

U.S. PATENT DOCUMENTS 5,554,154 A * 9/1996 Rosenberg ....... A61B 5/150519
606/167
6,033,408 A * 3/2000 Gage .................. A61B 17/1633
173/218
(Continued)

FOREIGN PATENT DOCUMENTS

CN 107405146 11/2017
EP 3 061 408 8/2016

OTHER PUBLICATIONS

International Search Report dated Jun. 1, 2021, for PCT/EP2021/055526, 3 pp.
(Continued)

*Primary Examiner* — Matthew J Lawson
(74) *Attorney, Agent, or Firm* — NIXON & VANDERHYE

(57) ABSTRACT

The present disclosure is in the field of surgical instrument, in particular drills used by surgeons and or dentist, or surgical robots. It is known that a motor generates a torque during rotating accelerations and decelerations. Accelerations and sharp brakes from powerful motors also generate torques to be countered by the surgeon wrist, or the robot chassis. In order to solve this problem, there is proposed a surgical power motor. The motor is made of two rotating parts, rotating in opposed directions, and further includes an inverter to link one rotating part with the other rotating part, each rotating part producing the similar acceleration torque and at least one being powered either by an electric or pneumatic source.

19 Claims, 3 Drawing Sheets

(56) References Cited

U.S. PATENT DOCUMENTS

| | | | | |
|---|---|---|---|---|
| 9,867,675 | B2* | 1/2018 | Beardsley | A61B 90/70 |
| 2005/0256512 | A1* | 11/2005 | Del Rio | A61B 17/1624 |
| | | | | 606/1 |
| 2008/0262526 | A1* | 10/2008 | Neubardt | A61B 17/1615 |
| | | | | 606/180 |
| 2013/0123783 | A1* | 5/2013 | Marczyk | A61B 18/1445 |
| | | | | 606/1 |
| 2015/0119889 | A1* | 4/2015 | Prescott | A61B 17/1679 |
| | | | | 606/80 |
| 2017/0150975 | A1* | 6/2017 | Bozung | A61B 17/1628 |
| 2019/0223957 | A1 | 7/2019 | Dekel et al. | |
| 2020/0222061 | A1* | 7/2020 | Hines | A61B 17/162 |
| 2022/0338895 | A1* | 10/2022 | Bono | A61B 17/1624 |
| 2023/0067104 | A1* | 3/2023 | Bono | A61B 17/1631 |
| 2024/0081931 | A1* | 3/2024 | Bono | A61B 34/30 |
| 2024/0156470 | A1* | 5/2024 | Barnes | A61B 17/1622 |

OTHER PUBLICATIONS

Written Opinion of the ISA dated Jun. 1, 2021, for PCT/EP2021/055526, 6 pp.

* cited by examiner

SURGICAL INSTRUMENT FOR DRILLING

This application is the U.S. national phase of International Application No. PCT/EP2021/055526 filed Mar. 4, 2021, which designated the U.S. and claims priority to EP 20161064.9 filed Mar. 4, 2020, the entire contents of each of which are hereby incorporated by reference.

INTRODUCTION

The present invention is in the field of surgical instrument, in particular drills used by surgeons and or dentist, or surgical robots. A surgical drill is an instrument used to bore or reduce bones, to provide access, or for the attachment of various implants, plates, or screws or to remove decay and reshape teeth in preparation for a filling. The devices are precision instruments accommodating a variety of drill attachments and bits to cater for a range of applications in anything from dental to neurological, ENT, or orthopedic surgeries.

Problem to be Solved

It is known that a motor generates a torque during rotating accelerations & decelerations. Dynamic Torque is made up of two components; an inertia component and a change of rotational speed component.

The acceleration (or deceleration) torque is acting on the motor when it is accelerating or decelerating. Once the motor is running at a constant speed, this component goes away.

When angled surgical high speed drills accelerates or brakes sharply drill's tips deviate, due to the acceleration (or deceleration) torque, and offset distance between the drill bit and the motor axis. Deviation will present a high risk of local tissues/bones damages.

Accelerations and sharp brakes from powerful motors also generate torques to be countered by the surgeon wrist, or the robot chassis. During lengthy drilling procedures, this can generate discomfort and reduce precision for the surgeon. When using surgery robots, the torque generates load on the axis systems, and can generate a deviation and temporarily reduced accuracy of the robotic system.

Even with navigation systems installed on hand-held drills, the navigation system will not be able to avoid the tip deviation generated by the motor accelerations & decelerations.

BRIEF DESCRIPTION OF THE INVENTION

In order to solve the problem mentioned above, it is proposed:

A surgical power motor, characterized in that, the motor is made of two rotating members, rotating in opposing directions, and further comprising an inverter to link one halve rotating member with the other one, at least one being powered either by an electric or pneumatic source.

The first feature is that the two parts have the same torque characteristics, i.e. when rotating, they produce the similar torque. Similar is to be understood that the difference between the two generated torques is little in the range below 25%. The torque is dependent of the mass of the motor's halve and the distance from the axis of rotation of the motor.

The second feature is that the two parts rotate in opposite direction.

The third feature is a coupler/inverter linking the two parts, at least one of which is directly or indirectly linked to the axis output of the motor assembly on which a tool can be mounted.

BRIEF DESCRIPTION OF THE FIGURES

The present invention will be better understood thanks to the attached figure in which.

DETAILED DESCRIPTION

Figure 1:
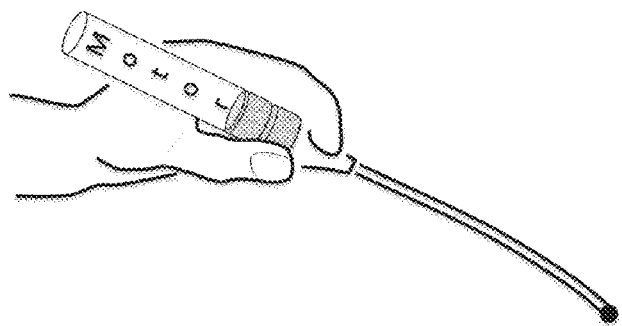
FIG. 1 illustrates a drill according to the prior art

The FIG. 1 illustrates a motor for surgical application which have one element producing the drilling torque. As explained above, each rotation speed variation of the motor produces a torque that the holder of the motor (hand or robot) should compensate.

According to the present invention, the motor of the drill comprises a first and a second part, each part rotating in a different direction. As a consequence, the inertia torque generated by one part cancels the inertia torque generated by the other one. The rotative parts being powered by either an electrical source or a pneumatic source.

The first and the second part form the motor assembly in charge of delivering a drilling torque for a surgical tool.

In a first embodiment, both parts participate to the drilling torque, the first part being connected with an inverter with the second part in order to produce the torque in the opposite rotating direction as the second part.

According to one embodiment, the two parts are identical in rotation speed, mass and size so that the acceleration torque of one part counter-balance the acceleration torque of the second part.

According to another embodiment, the two parts might have their specific rotation speed, mass and size as long as the acceleration torque produced by each part is of the same order of magnitude.

In a further embodiment, only one part is an active motor (the main part) and generates the drilling torque, the other part being a passive rotating element, playing only the role of acceleration torque cancellation, without providing additional power. Due to the presence of the inverter, the passive rotating element generates, while rotating, the same acceleration torque but in opposite direction. In this embodiment, the size, mass of the second part can be the same or different than the main part as long as the acceleration torque is the same as the acceleration torque of the main part.

Figure 2:
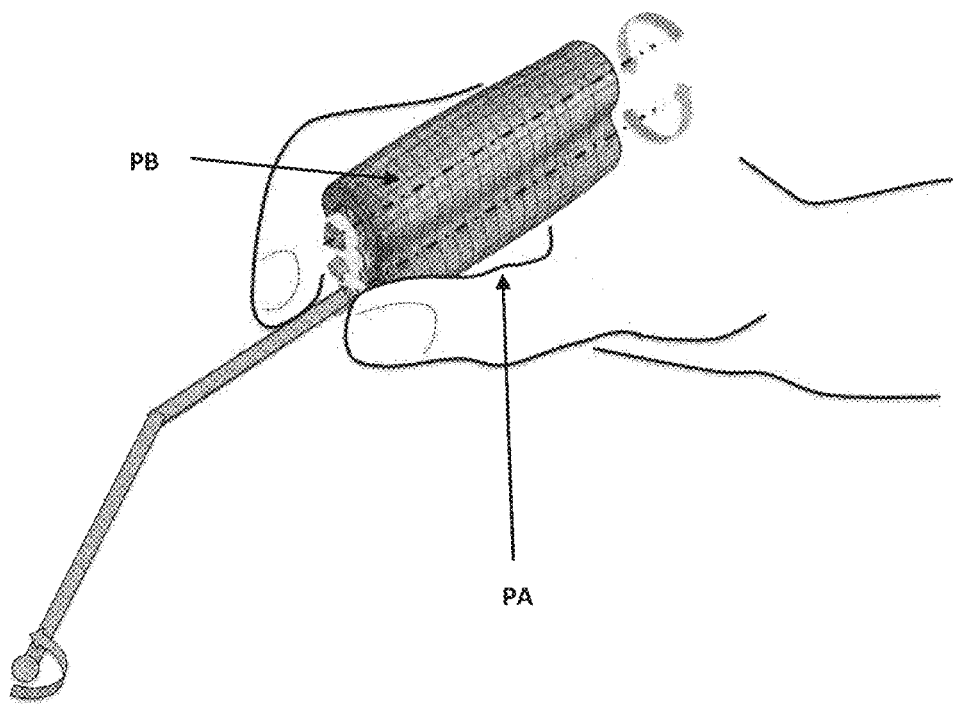
FIG. 2 illustrates a drill according to embodiment with 2 adjacent motors

Various arrangements of the first part and the second part can be realized. According to one version illustrated by the FIG. 2, both parts are mounted in parallel, side by side and connected by the inverter. In this example, the part PA and PB are two motors contributing to the generation of the drilling torque. The end of the axis of the second part PB is terminated by a gear engaged with another gear mounted on the axis of the first part PA. Both parts are rotating in opposite directions. The end of the first part PA is connected to the drill holding mechanism.

Figure 3:
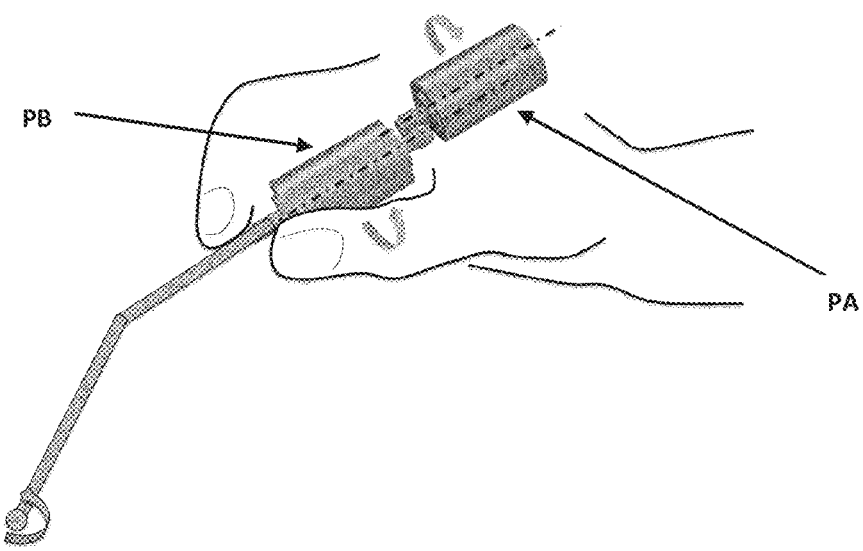
FIG. 3 illustrates the embodiment where the two rotative members are placed in front of each other.

In the example of the FIG. 3, the part PA and part PB are positioned one behind the other one. The axis of each part can be the same or, as it is illustrated, slightly different.

Figure 4:
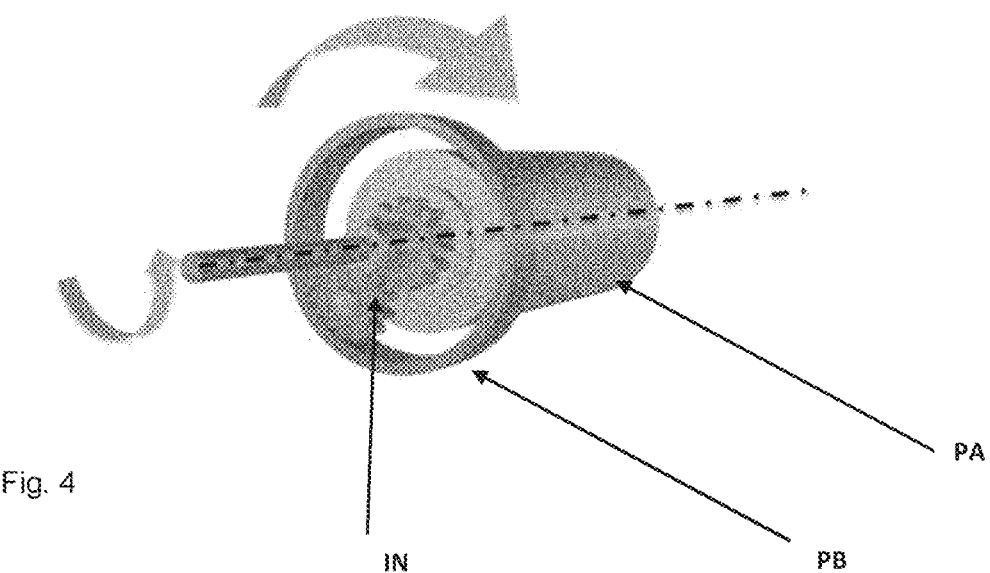
FIG. 4 illustrates another embodiment with a passive rotating element.

In the example of the FIG. 4, only the part PA contributes to the drilling force. This part is the motor. The part PB is in the shape of a ring having a different size and mass than the part PA. The part PB is designed to create the similar acceleration torque as the part PA. The inverter linking the part PA and part PB can be a simple rotation inverter with a speed ration 1:1 or a inverter having a different ratio. The ratio will be taken into account to determine the mass, size and position of the part PB in order to produce the similar acceleration torque.

Figure 5:
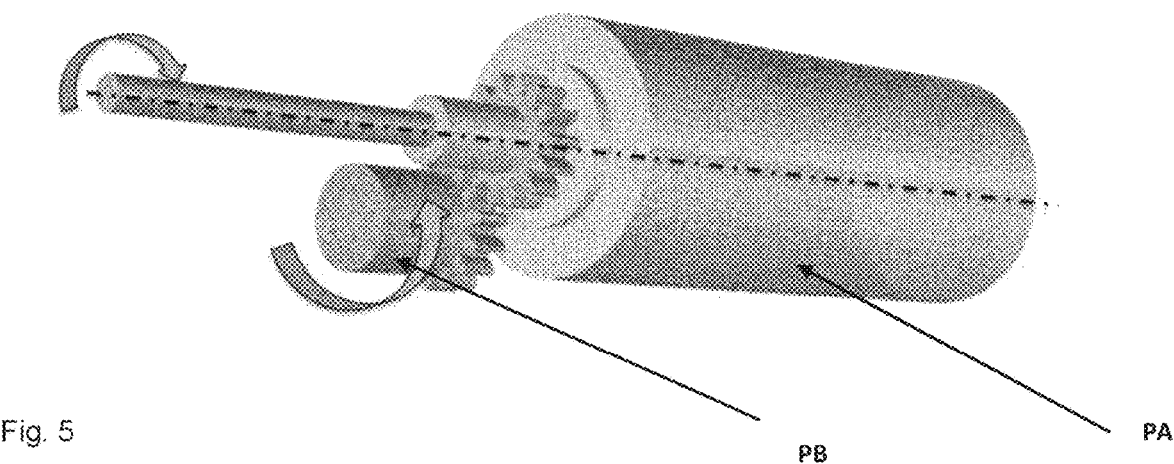
FIG. 5 illustrates another embodiment with a rotating mass.

In the example of the FIG. 5, we have another design with the part PB having a different axis as the part PA. The part PB is realized by an element in which the volume and mass is calculated to produce the same acceleration torque as the part PA.

Figure 6:
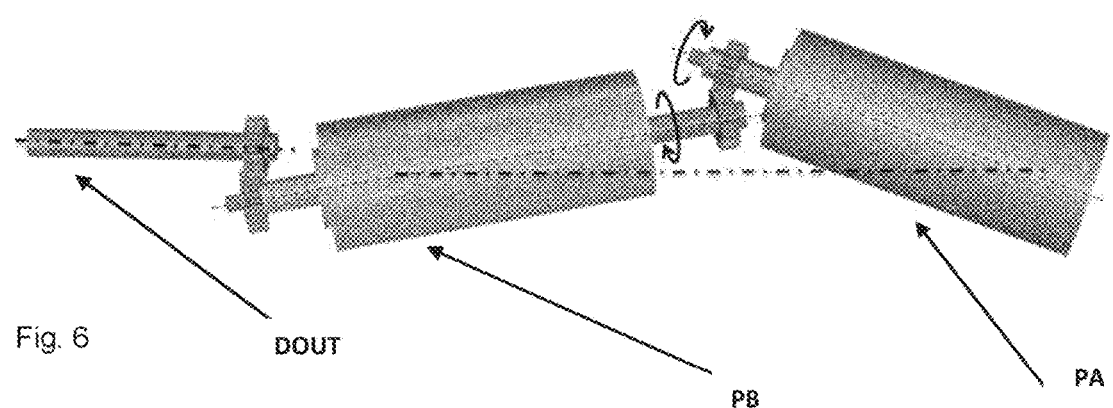
FIG. 6 illustrates an execution with non-parallel rotating parts

The FIG. 6 illustrates an example in which the axes of both parts are not parallel. With the axis in bold, we show the resulting axis of the combination of the acceleration torque. This axis is also preferably the axis of the drill output DOUT. The principle stays the same, one part PA generates an acceleration torque that is offset of the acceleration torque of the second part PB.

Figure 7:
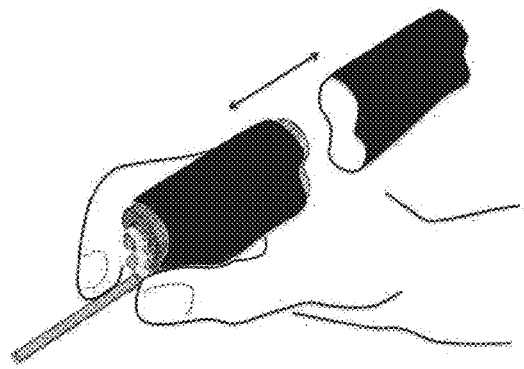
FIG. 7 illustrates a drill receiving a thermally-Insulating removable jacket

The FIG. 7 illustrates one embodiment with the rotating elements mounted side-by-side and in which a thermally insulated jacket is inserted. This jacket can be removed for washing for example. The first and the second part form the motor assembly. The removable jacket can be mounted, by sliding, around the motor assembly.

The invention claimed is:

1. A surgical power motor, comprising:
two rotating parts, rotating in opposed directions, each of the rotating parts producing a similar acceleration torque, at least one of the rotating parts being powered by one of an electric source and a pneumatic source;
an inverter to link one of the rotating parts with another one of the rotating parts; and
a holder configured to hold an attachable drill bit.

2. The surgical power motor of claim 1, wherein the one rotating part and the other rotating part are placed on a same or parallel axis.

3. The surgical power motor of claim 2, wherein the one rotating part is a motor and the other rotating part is a passive rotating element.

4. The surgical power motor of claim 3, wherein the first one rotating part and the other rotating part have the same size and mass.

5. The surgical power motor of claim 3, wherein the one rotating part and the other rotating part have a different size and mass.

6. The surgical power motor of claim 2, wherein the one rotating part is a first motor and the other rotating part is a second motor.

7. The surgical power motor of claim 6, wherein the one rotating part is a first motor and the other rotating part is a second motor, each of the first motor and the second motor being independently driven based on drilling conditions.

8. The surgical power motor of claim 7, wherein the drilling conditions are selected from the group consisting of heat-generated, vibrations detected, torques or torque variations detected, and speed fluctuations detected.

9. The surgical power motor of claim 4, wherein the one rotating part and the other rotating part have the same size and mass.

10. The surgical power motor of claim 6, wherein the one rotating part and the other rotating part have a different size and mass.

11. The surgical power motor of claim 2, wherein the one rotating part and the other rotating part have the same size and mass.

12. The surgical power motor of claim 2, wherein the one rotating part and the other rotating part have a different size and mass.

13. The surgical power motor of claim 2, wherein the one rotating part and the other rotating part are mounted side-by-side.

14. The surgical power motor of claim 1, wherein the one rotating part and the other rotating part have the same size and mass.

15. The surgical power motor of claim 1, wherein the one rotating part and the other rotating part have a different size and mass.

16. The surgical power motor of claim 1, wherein the one rotating part and the other rotating part are mounted side-by-side.

17. The surgical power motor of claim 1, wherein the one rotating part and the other rotating part are mounted one behind the other one.

18. The surgical power motor of claim 1, wherein the one rotating part is an active motor and the other rotating part is disposed around the one rotating part.

19. The surgical power motor of claim 1, further comprising a mountable- and removable-thermally-insulating jacket.

* * * * *